(12) United States Patent
Storer et al.

(10) Patent No.: US 6,626,948 B2
(45) Date of Patent: Sep. 30, 2003

(54) FEMORAL HIP PROSTHESIS

(75) Inventors: John Andrew Storer, Bayeux (FR); Richard Eddy Field, Walton-on-the-Hill (GB); Neil Rushton, Cambridge (GB)

(73) Assignee: Benoist Girard SAS (FR)

( * ) Notice: Subject to any disclaimer, the term of this patent is extended or adjusted under 35 U.S.C. 154(b) by 0 days.

(21) Appl. No.: 09/817,605

(22) Filed: Mar. 26, 2001

(65) Prior Publication Data

US 2002/0049501 A1 Apr. 25, 2002

(30) Foreign Application Priority Data

Mar. 27, 2000 (GB) .............................................. 0007392

(51) Int. Cl.$^7$ ................................................. A61F 2/32
(52) U.S. Cl. .................................. 623/23.14; 623/23.15
(58) Field of Search ........................... 623/23.11–23.15, 623/23.18, 23.21–23.24, 23.29–23.31, 23.32, 23.33, 23.42, 23.36, 23.57, 23.58, 23.6, 19.11, 19.12

(56) References Cited

U.S. PATENT DOCUMENTS

| | | | | |
|---|---|---|---|---|
| 2,685,877 A | * | 8/1954 | Doublle ........................ 411/21 |
| 4,146,936 A | * | 4/1979 | Aoyagi et al. ............. 427/2.27 |
| 4,532,660 A | | 8/1985 | Field ............................ 623/18 |
| 4,662,888 A | | 5/1987 | Field ............................ 623/16 |
| 4,846,839 A | * | 7/1989 | Noiles ...................... 623/23.46 |
| 4,976,740 A | * | 12/1990 | Kleiner ..................... 623/23.14 |
| 5,314,492 A | * | 5/1994 | Hamilton et al. ......... 623/23.34 |
| 5,702,448 A | * | 12/1997 | Buechel et al. ............... 606/65 |
| 5,906,644 A | * | 5/1999 | Powell ..................... 623/20.15 |

FOREIGN PATENT DOCUMENTS

| | | |
|---|---|---|
| FR | 1 107 877 | 1/1956 |
| FR | 299 400 | 6/1994 |
| GB | 719 308 | 12/1954 |
| WO | WO 98/07393 | 2/1998 |

* cited by examiner

*Primary Examiner*—Kevin Shaver
*Assistant Examiner*—Michael B. Priddy
(74) *Attorney, Agent, or Firm*—Lerner, David, Littenberg, Krumholz & Mentlik, LLP

(57) ABSTRACT

A prosthetic femoral component is located in a prepared socket in a femur which has been resected at a position on the proximal side of its neck. The component includes an insert portion and an enlarged proximal head portion the distal end of the head portion being adapted for location in the prepared socket. The component takes advantage of the bone at the periphery of the socket which enables the insert and the part of the head concerned to be accurately and firmly located in the bone. The presence of the bone at the outer edges of the socket helps to stabilize the component. The insert portion can be dimensioned to pass through the neck of the femur with which it is to be used or to be shorter depending upon the requirements.

31 Claims, 2 Drawing Sheets

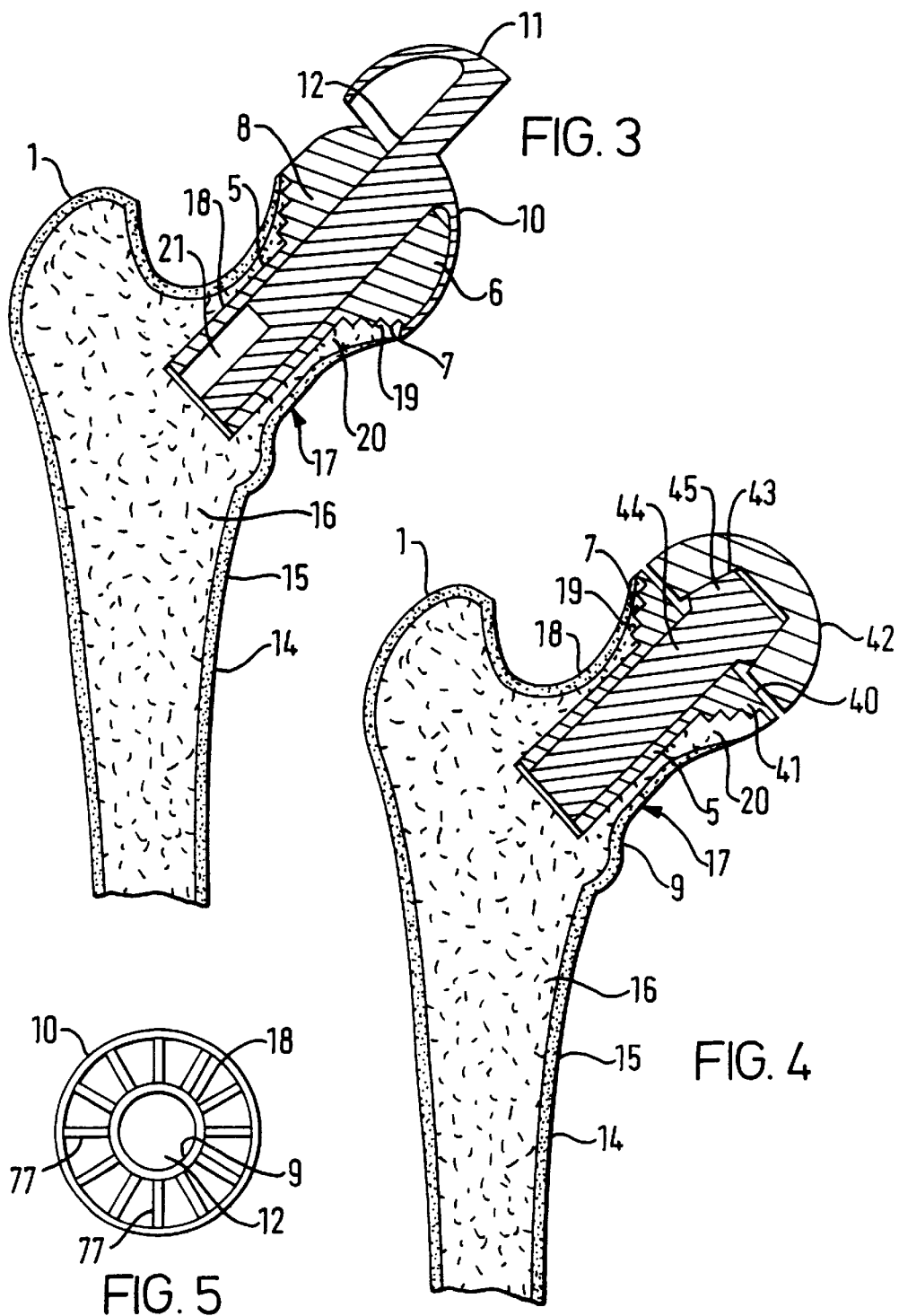

FEMORAL HIP PROSTHESIS

BACKGROUND OF THE INVENTION

This invention relates to a prosthetic femoral component of the type which is applied without a stem in the medullary canal, which component is considered to be conservative and bone sparing.

For present purposes a conservative femoral hip prosthesis is a prosthesis which leaves sufficient bone in place for it to be eventually replaced by a more conventional femoral hip prosthesis with a medullary stem normally intended for primary (non-revision) application. A bone-sparing femoral hip prosthesis is one which limits the removal of viable bone by conserving some of the femoral head, removing only sufficient bone to resect the diseased tissue and to effect a satisfactory anchorage.

The use of femoral hip prostheses which function without a stem in the medullary canal date from the first total hip prosthesis reported by Wyles in 1937. This hip prosthesis was fitted following a high resection of the femoral head and was stabilized with a straight stem which passed along the femoral neck and out below the greater trochanter, where it was attached to a bone plate secured on the lateral cortex of the femur. The Wyles hip restored the femoral head with a bearing diameter deliberately smaller than the natural femoral head it was replacing. Only six cases were ever performed using this device since the clinical outcome was not impressive.

Another femoral hip prosthesis design following that of Wyles was the Judet prosthesis, developed in France and used in the period 1945–55. A high neck resection was used with this prosthesis, which attempted to restore the femoral head to its natural diameter for use as a hemiarthroplasty. The prosthesis comprised an acrylic (low modulus) head and a short straight stem which passed along the femoral neck. The prosthetic head included a trough around the stem attachment to the head, which was used to seat and locate the prosthesis on the prepared proximal end of the femoral neck. Early breakage caused the stem to be given a stainless steel core support. Later failures saw the device breaking out through the inferior femoral neck. All versions of this prosthesis suffered from premature wear of the acrylic head.

High neck resections, i.e. those conserving the femoral neck, were also used by femoral hip prostheses with stems passing into the medullary canal, notably the designs of Pipino (1978) and Freeman (1985). These hip prostheses were implanted both cement-free and with cement, but did not attempt to restore the femoral head to its natural diameter, being used as total hip replacements with a head of smaller dimensions. Since these femoral hip replacements do place a stem in the medullary canal, they are not considered to be conservative, although the stem on the Pipino design was very short.

Designs of femoral hip prostheses which have attempted to secure the replacement of the femoral head without a stem in the medullary canal follow the design of Vincent and Munting reported in 1982, which is still in clinical use. With this design, a portion of the femoral neck is preserved and shaped with a notch to provide seating for the implant. The prosthesis is used as a total hip replacement and replaces part of the femoral neck and the femoral head with a head of smaller diameter than the natural head. The prosthesis is used uncemented and is fixed with a large screw through the lateral cortex into the body of the prosthesis. The prosthesis is intended to sit on the remaining cortex of the neck and is stabilized by fins parallel to the axis of the neck which pass into the remaining diaphyseal cancellous bone. The bone engaging surfaces are provided with a hydroxyapatite coating to promote bone ongrowth to augment fixation.

The Vincent-Munting prosthesis is considered to be conservative but not bone sparing, according to the definitions given above. The only type of femoral hip prosthesis which has been developed which is conservative and bone sparing is the femoral cap used in prostheses such as the ICLH (Freeman, 1973), the THARIES (Amstutz, 1976), the Wagner (Wagner, 1973), the Zephyr (Aubriot, 1977) and the Gérard (Gérard, 1975). This type of prosthesis comprised a metal cap with a part-spherical external form and different internal forms and was used both cemented and uncemented. The bearing surface of the femoral cap was always near to anatomical size, therefore the cap could be used as a hemiarthroplasty. Mechanical loosening through stress concentration at the bone interface were reported as well as resorption of epiphyseal bone beneath the cap. The cause of the bone resorption was associated with disruption of the blood supply to regions of bone as a result of the surgical technique. Often the cap was used to articulate with a polyethylene liner in the acetabulum, and with this an additional failure mode of osteolysis at the bone interface with the prosthesis was caused by the ingress of polyethylene debris.

A development of the femoral cap design was the inclusion of a short stem to the cap. Examples of such designs include the TARA hip (1970's) and, more recently the McMinn hip (1990's).

An alternative design approach for the femoral cup is presented in U.S. Pat. Nos. 4,532,660 and 4,662,888, which describe a stemless femoral hip prosthesis intended to load the bone naturally. The first design required the resection of most the femoral head and part of the neck, the later design required only the resection of the proximal portion of the femoral head up to the epiphyseal scar plate. In the later design, a low modulus material between the bone and the femoral cap was used to transfer load with a more physiological force distribution onto the trabecular structure of the proximal femur. In practice, too little bone was removed for adequate surgical exposure of the acetabulum without excessive soft tissue damage. Furthermore, controlled exposure of the three-dimensional epiphyseal scar plate proved to be too complex and the design was never developed into an implant.

Cemented intramedullary fixation of femoral hip prostheses has now approximately 30 years successful clinical results and is the benchmark against which new designs of hip implants are assessed. Early problems of implant fracture, corrosion, cement mantle integrity and excessive bearing wear have now been largely resolved and the main problem which limits the life expectancy of conventional femoral hip prosthesis is aseptic loosening. Nevertheless, since premature failure of the reconstruction may occur due to loosening, eventual revision of the prosthesis, particularly when used for younger patients (under 65), must be considered.

The revision of cemented stemmed femoral hip prostheses is challenging, particularly as a result of needing to remove all the cement. In fact, cementless stems with intramedullary fixation have been developed to simplify the revision procedure. Such devices require increased surgical precision compared with cemented hip prostheses and have their own failure modes such as pain, loosening and subsidence.

It is the likelihood of subsequent revision for the younger and more active patient which makes a conservative, and indeed bone sparing, femoral hip prosthesis an attractive option. In theory, such a device may be revised with a conventional primary stemmed hip prosthesis without the need for bone grafting or other augmentation. Indeed, there is no reason why conservative hip designs could not be at least as safe and efficacious as intramedullary stemmed hip designs. However, attempts so far to develop a conservative, bone sparing femoral hip prosthesis have encountered significantly worse results due to premature loosening of the femoral component (and acetabular component).

The present design seeks to provide a conservative, bone sparing femoral hip prosthesis that addresses the problems encountered by previous designs. The prosthesis includes an insert portion which is designed to control the transfer of load to the femur so as to avoid stress concentration at the bone interface. The insert portion is sized so that it replaces all the epiphyseal bone thereby minimizing the risk of bone resorption due to disrupted blood supply. It is also tapered so as to self seal under load so as to restrict the ingress of debris leading to osteolysis.

In addition to addressing the deficiencies of previous designs, the present design seeks to simplify the surgical technique so as to achieve better reproductability of results to minimize the trauma (e.g. loss of blood, post-operative infection) associate with the procedure.

Hip replacement is usually performed with a large exposure. Early post-operative infection is no longer a significant problem, but the time to heal such a major wound is significant. Some surgeons now implant conventional stemmed devices with as small an incision as they possibly can. After the femoral head and neck have been removed, only narrow tools are needed to prepare the femoral canal and there is easy access to the acetabulum. However, the bone sparing femoral hip prosthesis designs generally necessitate reverting to a wider exposure for two reasons. Firstly, preparation of the outside of the femoral head involves bulkier instruments. Secondly, the femoral head obstructs access to the acetabulum. More cutting of soft tissues attaching the femur to the pelvis is needed to maneuver the femoral head out of the way.

SUMMARY OF THE INVENTION

The present invention is intended to provide a femoral hip prosthesis which can be employed in a method of fitting which includes cutting away the natural femoral head to expose the circular cross-section of the neck at the base of or at a mid point of the head. This allows much improved access to the acetabulum, thereby reducing the length of the required incision and minimizing the soft tissue dissection necessary to allow the remaining femoral head to be levered out of the way. The shape of the insert portion of the prosthesis is designed so as to allow it to be fitted to the bone accurately following a simple, non-bulky, reproducible reaming operation. As such, the close fit will resist micromotion and act in support of the self-sealing taper design to impede the ingress of debris. The fact that non-bulky instruments may be used allows a less invasive surgical technique to be employed.

According to the present invention a prosthetic femoral component for location in a prepared socket in a femur which has been resected at a position on the proximal side of its neck includes an insert portion and an enlarged proximal head portion the distal end of the head portion being adapted for location in the prepared socket.

Thus, the component according to the present invention takes advantage of the bone at the periphery of the socket which enables the insert and the part of the head concerned to be accurately and firmly located in the bone. The presence of the bone at the outer edges of the socket helps to stabilize the component.

The insert portion can be dimensioned so that it is adapted to pass through the neck of the femur with which it is to be used or to be shorter depending upon the requirements.

Preferably the proximal end of the head portion is adapted to receive a substantially part spherical bearing element and with this construction the insert portion can be made from any suitable material. Preferably the bearing element is provided with an elongate spigot or trunnion which can engage in a bore in said head portion. If desired the spigot can be arranged to extend through the head portion and into the insert portion.

With the arrangement described above the spigot can be dimensioned and adapted to enlarge the outer dimensions of the insert portion to expand it into tight engagement in the bone in which it is to be fitted. In any case, the proximal end of the head portion can be substantially hemispherical and the bearing element can be hollow to closely surround it when in position. With this arrangement the spigot can be integral with the bearing element.

In any alternative construction the proximal end of the head portion is substantially flat and the bearing element is formed by a substantially solid part spherical member provided with said spigot. The substantially part spherical member can be made from a ceramic material, for example alumina, zirconium or zirconium toughened alumina.

If desired the spigot can thus be formed from a different material from the bearing element and be attached thereto, for example, the spigot can be formed from metal and the bearing element from a ceramic material.

If desired the distal side of the head portion where it joins the insert portion can be formed as a series of radially projecting steps or fins.

BRIEF DESCRIPTION OF THE DRAWINGS

The invention can be performed in various ways and some embodiments will now be described by way of example and with reference to the accompanying drawings in which:

FIG. 3 is a cross-sectional view through a femur with the femoral component of FIG. 2 shown in a part inserted and fully inserted position;

FIG. 4 is a cross-sectional side elevation of a femur showing an alternative construction according to the invention; and FIG. 5 is an end view of the construction shown in FIG. 2 utilizing an alternative head portion construction.

DETAILED DESCRIPTION OF THE PREFERRED EMBODIMENTS

Figure 1:
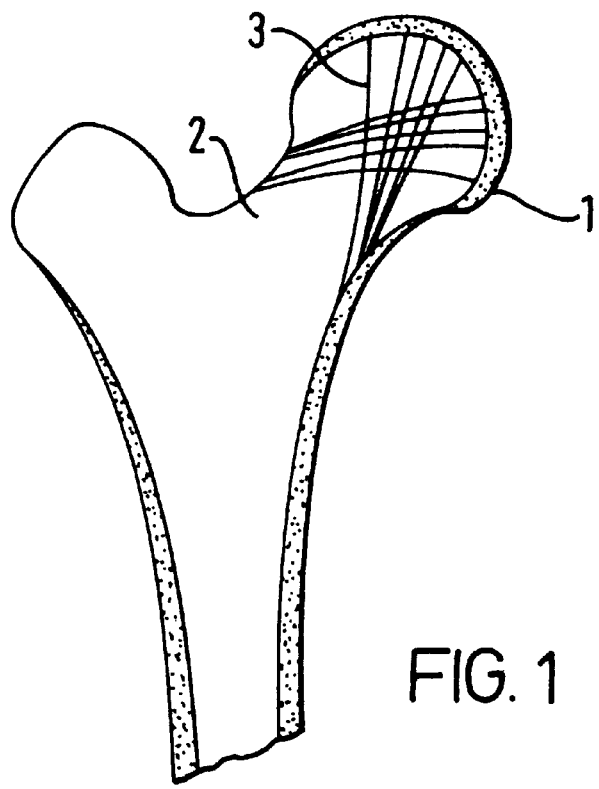
FIG. 1 is a diagrammatic view of the proximal end of a femur showing the general construction of the bone and the trabecular fibers.

As shown in FIG. 1 the natural construction of a femur consists of an outer hard bone, usually referred to as the cortex, which in the region of the ends of the femur encases a spongy interior. The cortex extends over the head of the femur, indicated by reference numeral 1, but is very thin at the junction of the head 1 and the neck 2. Trabecular fibers, indicated by reference numeral 3, sprout from the cortex upwardly and through the head 1, as shown in FIG. 1. It has been observed that, if the bone is cut, these fibers are best able to reform around sharp surfaces.

Figure 2:
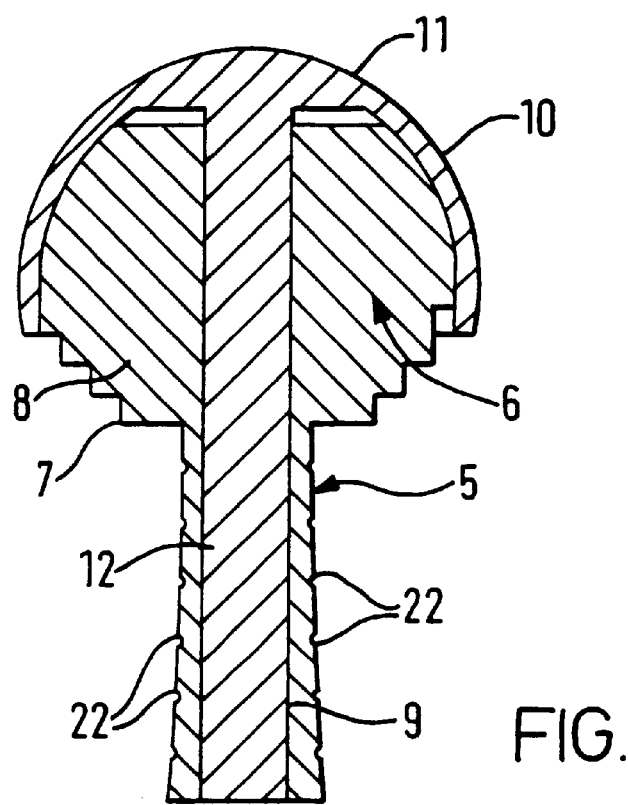
FIG. 2 is a cross-sectional view of a prosthetic femoral component according to the invention.

FIG. 2 shows a preferred prosthetic femoral component according to the present invention and this comprises an insert portion 5 adapted for location in a prepared socket in the femur in which it is to be fitted and an enlarged proximal head portion 6, the distal part 8 of which is also intended to be located in the socket. In the preferred embodiment the distal part 8 of the head portion 6 is formed as a series of radially projecting steps 7 which act as means to encourage the reformation of the trabecular fibers in that region. A bore 9 extends through the head portion 6 and into the insert portion 5.

A bearing element 10 is provided which can be made from metal or any other suitable material and this comprises a part-spherical bearing ball 11 which is adapted to extend over the head portion 6. The bearing ball 11 is hollow and extending from it is an elongate spigot 12 which is dimensioned and adapted to pass through the bore 9 in the head portion 6 and into the insert portion 5.

The distal portion of the bore 9 in the insert portion 5 is tapered inwardly as will be seen most clearly at the left hand side of FIG. 3 from the tapering thickness of the side walls. As the spigot 12 is pressed inwardly it causes the side walls of the insert portion 5 to expand outwardly to the position shown at the right hand side of FIG. 2 and FIG. 4.

Inspection of FIG. 3 will show the taper extending inwardly before the ball 11 is pressed completely into position.

The spigot or trunnion 12 is integral with the hollow ball 11.

FIG. 3 shows the preferred prosthetic femoral component in position in a femur indicated by reference numeral 14. The cortex is indicated by reference numeral 15 and the spongy interior by reference numeral 16. In order to apply the prosthetic femoral head the natural head is resectioned immediately above the neck 17 of the femur and is cut to provide a bore 18, the proximal end of which is enlarged using a reamer to provide a series of radially inwardly extending steps 19. It is important to cut the bone above the base of the femoral head thereby retaining the maximum amount of trabecular fibers which are indicated by reference numeral 20.

The preferred insert portion 5 and the head portion 6 can be made of any suitable materials, for example a synthetic plastic material such as a synthetic resin and carbon fibers, typical examples being PEEK (polyetheretherketone) or PBT (polybutalieneterephthalate) resin into which a chopped carbon fiber can be incorporated. Preferably the material is of a similar compressive modulus as cancellous bone.

When the insert portion 5 is pressed into position it will be seen that the steps 7 are aligned and co-operate with the steps 19 in the bone. This encourages growth of the trabecular fibers to reform around the sharp corners of the steps thus assisting in relaying loads from the bearing element provided by the ball 11 to the cortex 15.

The bearing element 10, in the form of the part spherical bearing ball 11, is shown in two different positions in FIG. 3. In the upper position it is partly inserted down to the point where its spigot 12 is about to engage the tapered portion 21 of the bore 9. As the ball 11 is pushed further into position it causes the outer circumference of the insert portion 5 to expand outwardly into the soft core of the bone. In order to assist in providing a grip the insert portion 5 carries a series of circular indentations 22 (most clearly seen in FIG. 2).

When the ball head 11 is fully in place it closely surrounds the head portion 6 and can transmit loads through it.

FIG. 5 shows an alternative construction in which the radially projecting steps 7 are replaced by radially projecting fins 77 intended to achieve the same effect.

FIG. 4 shows an alternative construction and the same reference numerals are used to indicate similar parts. In this arrangement the proximal end 40 of the head portion 41 is substantially flat and a bearing element is formed by a substantially solid part-spherical member 42. This is provided with a tapered blind bore 43 to accept a spigot or trunnion 44 provided with a suitably tapered boss 45. A Morse taper is provided between the parts so that they lock together when in position. The member 42 is made from a ceramic material, for example alumina zirconium or zirconium toughened alumina, and the spigot 44 is metal. The spigot 44 engages in the insert portion 5 in a similar manner to that described with regard to FIGS. 2 and 3.

As mentioned above, in the preferred embodiment the insert portion 5 and the head portion 41 can be made from a synthetic plastics material and this can be coated with plasma sprayed hydroxyapatite (HA) coating which is osteoconductive and stimulates bone growth. Alternatively they could be made from metal, for example, titanium, with a porous coating such as a coating as set forth above.

In all the above constructions the surface finish of parts which abut bone can be in the form of a cut-away honeycomb.

The insert portion can be made from any of the materials referred to above and again be coated with plasma sprayed hydroxyapatite (HA) which is osteo-conductive and stimulates bone growth. If desired it could be made from metal, for example, titanium, with a porous coating such as a coating as set forth above.

In the constructions described above the insert portion is driven into the bone but it could be held by cement. Thus a small amount of cement could be applied at the proximal end of the insert portion, bone growth being relied upon towards the distal end.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A prosthetic femoral component for location in a prepared socket in a femur which has been resected at a position on the proximal side of its neck, comprising an insert having and an enlarged proximal head portion, a distal portion of said insert being adapted to pass through said neck for location in said prepared bone socket and a part-spherical bearing element for engaging the proximal head portion of said insert, said bearing element is provided with an elongate spigot which can engage in a bore provided in said head portion, said spigot extends through said head portion and into the distal insert portion, said spigot is dimensioned and adapted to enlarge the outer dimensions of the distal insert portion to expand it into tight engagement in the bone in which it is to be fitted.

2. The prosthetic femoral component as claimed in claim 1 in which the insert portion is dimensioned so that it is adapted to pass through the neck of the femur with which it is to be used.

3. The prosthetic femoral component as claimed in claim 1 in which a distal portion of the bore in said head portion is tapered inwardly to cause side walls of the distal insert portion to expand outwardly when the spigot is inserted.

4. The prosthetic femoral component as claimed in claim 3 in which the proximal head portion has a proximal end which is substantially hemispherical and the bearing element is hollow to closely surround it when in position.

5. The prosthetic femoral component as claimed in claim 4 in which said spigot extends through said head portion and into the insert portion.

6. The prosthetic femoral component as claimed in claim 3 in which the proximal head portion has a proximal end which is substantially flat and the bearing element is formed by a substantially solid part-spherical member provided with said spigot.

7. A prosthetic femoral component as claimed in claim 6 in which said substantially solid part-spherical member is made from a ceramic material.

8. A prosthetic femoral component as claimed in claim 7 in which the ceramic material is alumina, zirconium or zirconium toughened alumina.

9. The prosthetic femoral component as claimed in claim 6 in which said spigot is provided with a tapered boss adapted to engage in a tapered bore in the part-spherical bearing element.

10. The prosthetic femoral component as claimed in claim 6 in which said spigot is formed from a different material from the bearing element and attached thereto.

11. The prosthetic femoral component as claimed in claim 10 in which the spigot is formed from metal and the bearing element from a ceramic material.

12. The prosthetic femoral component as claimed in claim 1 in which a distal part of the head portion adjacent the distal insert portion is formed as a series of radially projecting steps or fins.

13. The prosthetic femoral component as claimed in claim 12 in which the insert portion and the head portion are made of a synthetic plastics material.

14. The prosthetic femoral component as claimed in claim 13 in which the synthetic plastics material are PEEK (polyetheretherketone) or PBT (polybutalieneterephthalate) resin into which a chopped carbon fibre is incorporated.

15. The prosthetic femoral component as claimed in claim 14 in which the synthetic plastics material is of a similar compressive modulus as cancellous bone.

16. The prosthetic femoral component as claimed in claim 1 in which bone contacting parts of said insert are coated with plasma sprayed hydroxyapatite.

17. The prosthetic femoral component as claimed in claim 16 in which the insert is made from titanium and has a surface provided with a porous coating of plasma sprayed hydroxyapatite.

18. The prosthetic femoral component as claimed claim 1 in which the insert has bone contacting parts the surfaces of which are in the form of a cut-away honeycomb.

19. The prosthetic femoral component as claimed in claim 1 in which the insert is adapted to be driven into the bone.

20. The prosthetic femoral component as claimed in claim 1 in which said insert is adapted to be held in the bone by cement.

21. A femoral implant for implantation on a resected head of a femur, comprising:

a first member having a part-spherical outer bearing surface with a shaft extending from an inner surface of said first member; and a second member having a head portion and an insert portion with an internal bore extending along a longitudinal axis for receiving said shaft extending from said inner surface of said first member and a distally facing stepped bone contacting surface having a plurality of steps for engaging the head of the femur, said steps of said bone contacting surface extending at greater radially outwardly distances from said axis on moving in the distal to proximal direction, said internal bore of said second member is tapered inwardly on moving from the proximal to distal direction and wherein said shaft has a diameter greater than a diameter of a distal portion of said tapered internal bore such that a wall of said insert portion surrounding said internal bore extending distally of said stepped portion expands radially outwardly.

22. The femoral implant as set forth in claim 21, wherein an outer surface of said wall of said insert portion has a series of indentations extending about a circumference thereof.

23. The femoral implant as set forth in claim 21 wherein said steps extend in a circle about said longitudinal axis of said bore.

24. The femoral implant as set forth in claim 23 wherein said steps include portions which extend perpendicular and parallel to said axis meeting at right angles to form sharp corners.

25. The femoral implant as set forth in claim 21 wherein said second member is made of a non-metallic synthetic material.

26. The femoral implant as set forth in claim 25 wherein said material is a carbon fiber reinforced resin.

27. The femoral implant as set forth in claim 21 wherein said first member has a proximal portion with said part spherical outer bearing surface thereon, said proximal portion and said shaft are separate elements coupled together.

28. The femoral implant as set forth in claim 27 wherein said proximal portion and said shaft are coupled by a tapered connection.

29. A method of resurfacing a head of a femur comprising:

resecting the femur head immediately above the neck;

cutting a central bore in the remainder of the femur head;

forming a series of radially extending steps in the remaining resected head of the femur;

placing an insert portion having radially extending steps thereon in said bore in said head such that said implant steps are aligned and co-operate with the steps on the resected head of the femur; and placing a part-spherical bearing element on said insert portion.

30. The method as set forth in claim 29, wherein said insert portion has a distal shaft with a tapered bore and said bearing element has a shaft for engaging said bore.

31. The method as set forth in claim 30 further including expanding the side walls of the shaft of the insert portion by inserting the shaft of the bearing element in said bore to attach the insert portion to the femur.

* * * * *

UNITED STATES PATENT AND TRADEMARK OFFICE
CERTIFICATE OF CORRECTION

PATENT NO.     : 6,626,948 B2                                               Page 1 of 1
DATED          : September 30, 2003
INVENTOR(S)    : John Andrew Storer, Richard Eddy Field and Neil Rushton It is certified that error appears in the above-identified patent and that said Letters Patent is hereby corrected as shown below:

<u>Title page,</u>
Item [75], Inventors, "Walton-on-the Hill" should read -- Surrey --.
Item [57], ABSTRACT,
Line 4, after "portion" (second occurrence) insert -- , --.

<u>Column 1,</u>
Line 20, "date" should read -- dates --.

<u>Column 2,</u>
Line 17, "were" should read -- was --.
Line 35, after "most" insert -- of --.

<u>Column 3,</u>
Line 25, "associate" should read -- associated --.
Line 64, after "portion" (first occurrence) insert -- , --.

<u>Column 5,</u>
Line 37, after "head" (first occurrence) insert -- , --.

<u>Column 6,</u>
Line 53, cancel "and".

<u>Column 8,</u>
Line 59, "the side walls" should read -- sidewalls --.

Signed and Sealed this

Tenth Day of February, 2004

JON W. DUDAS
*Acting Director of the United States Patent and Trademark Office*